(12) United States Patent
Newkirk

(10) Patent No.: US 7,073,765 B2
(45) Date of Patent: Jul. 11, 2006

(54) APPARATUS FOR CARRYING MEDICAL EQUIPMENT

(75) Inventor: David C. Newkirk, Lawrenceburg, IN (US)

(73) Assignee: Hill-Rom Services, Inc., Wilmington, DE (US)

(*) Notice: Subject to any disclaimer, the term of this patent is extended or adjusted under 35 U.S.C. 154(b) by 183 days.

(21) Appl. No.: 10/700,501

(22) Filed: Nov. 5, 2003

(65) Prior Publication Data
US 2004/0164220 A1 Aug. 26, 2004

Related U.S. Application Data

(60) Provisional application No. 60/425,915, filed on Nov. 13, 2002.

(51) Int. Cl.
F16M 13/00 (2006.01)
(52) U.S. Cl. .................................. 248/647; 248/283.1
(58) Field of Classification Search ................ 248/647, 248/676, 282.1, 283.1, 343, 317; 5/600, 5/658, 503.1; 280/35
See application file for complete search history.

(56) References Cited

U.S. PATENT DOCUMENTS

| | | | |
|---|---|---|---|
| 4,130,123 A | 12/1978 | Wines, Jr. et al. | |
| 4,252,297 A | 2/1981 | Swain | |
| D261,804 S | 11/1981 | Foster et al. | |
| 4,452,499 A | 6/1984 | Verburg | |
| 4,572,594 A | 2/1986 | Schwartz | |
| 4,607,897 A * | 8/1986 | Schwartz | 312/209 |
| 4,610,118 A | 9/1986 | Fullenkamp | |
| 4,993,683 A | 2/1991 | Kreuzer | |
| 5,007,688 A | 4/1991 | Bayerlein et al. | |
| 5,040,765 A | 8/1991 | Schonfelder | |
| 5,072,906 A | 12/1991 | Foster | |
| 5,107,636 A | 4/1992 | Schindele et al. | |
| 5,186,337 A | 2/1993 | Foster et al. | |
| 5,207,642 A | 5/1993 | Orkin et al. | |
| 5,284,255 A | 2/1994 | Foster et al. | |
| 5,299,338 A | 4/1994 | Foster | |
| 5,344,169 A | 9/1994 | Pryor et al. | |
| 5,348,324 A | 9/1994 | Trotta | |
| 5,377,371 A | 1/1995 | Foster | |
| 5,398,359 A | 3/1995 | Foster | |
| 5,452,807 A | 9/1995 | Foster et al. | |
| 5,455,975 A | 10/1995 | Foster | |
| 5,590,648 A | 1/1997 | Mitchell et al. | |
| 5,605,344 A | 2/1997 | Insalaco et al. | |
| 5,618,090 A | 4/1997 | Montague et al. | |
| 5,842,238 A | 12/1998 | Herrick et al. | |
| 5,890,687 A | 4/1999 | Pryor et al. | |
| 5,918,841 A | 7/1999 | Sweere et al. | |
| 5,966,760 A | 10/1999 | Gallant et al. | |
| D418,603 S | 1/2000 | Gallant | |
| 6,073,285 A | 6/2000 | Ambach et al. | |

(Continued)

FOREIGN PATENT DOCUMENTS

DE  297 20 449 U 1  11/1997

(Continued)

Primary Examiner—Ramon O Ramirez
(74) Attorney, Agent, or Firm—Barnes & Thornburg LLP

(57) ABSTRACT

A patient care apparatus is disclosed for use with a patient. The patient care apparatus is configured to support equipment for care of the patient. An illustrative patient care apparatus has a suspension system and a pair of modules that are coupleable together to form a cart and that are separable for attachment to different portions of the suspension system.

20 Claims, 17 Drawing Sheets

| U.S. PATENT DOCUMENTS | | | | FOREIGN PATENT DOCUMENTS | | |
|---|---|---|---|---|---|---|
| D434,502 S | 11/2000 | Gallant | | EP | 0 903 141 A1 | 12/1997 |
| 6,213,481 B1 | 4/2001 | Marchese et al. | | EP | 0 867 134 B1 | 1/1998 |
| 6,343,601 B1 | 2/2002 | Kiske et al. | | WO | WO 96/35403 | 11/1996 |
| 6,360,389 B1 | 3/2002 | Gallant et al. | | | | |
| 2003/0014817 A1* | 1/2003 | Gallant et al. | 5/600 | * cited by examiner | | |

…

APPARATUS FOR CARRYING MEDICAL EQUIPMENT

CROSS-REFERENCE

This application claims the benefit under 35 U.S.C. §119(e) of U.S. Provisional Patent Application No. 60/425,915 which was filed Nov. 13, 2002 and which is hereby incorporated by reference herein.

BACKGROUND OF THE INVENTION

The present disclosure relates to patient care apparatus including apparatus for carrying medical equipment to provide medical services for delivery to a patient and/or to provide monitoring of physiological parameters of a patient.

In a healthcare environment, medical equipment is sometimes coupled to or carried by columns, arms, or carts. See, for example, the devices shown in U.S. Pat. Nos. 4,993,683; 5,007,688; 5,040,765; 5,072,906; 5,107,636; 5,186,337; 5,207,642; 5,452,807; 5,618,090; 5,966,760; 6,073,285; 6,213,481; and 6,343,601.

SUMMARY OF THE INVENTION

A patient care apparatus is provided for care of a patient and has one or more of the following features or combinations thereof, which alone or in any combination may comprise patentable subject matter:

The patient care apparatus may comprise a suspension system and a pair of modules. The modules may be coupleable together to form a cart and may be separable for attachment to different portions of the suspension system. The modules may be used to support medical equipment. For example, one of the modules may support IV equipment and the other module may support ventilation equipment.

The suspension system may be mounted to a ceiling and used to suspend the modules above the floor. The suspension system may be movable to move the modules horizontally and vertically. Such movement may be useful to stack the modules one on top of the other to form the cart and to unstack the modules.

The suspension system may comprise a pair of carriers, one for each module to carry the module. Each carrier may comprise a double-articulating arm system comprising a pair of arms pivotable about vertical axes. A service column configured to provide one or more services for care of the patient may be suspended from one of the pivot arms. Lifters attached to the service columns may be used to raise and lower the modules.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION OF THE DRAWINGS

Figure 1:
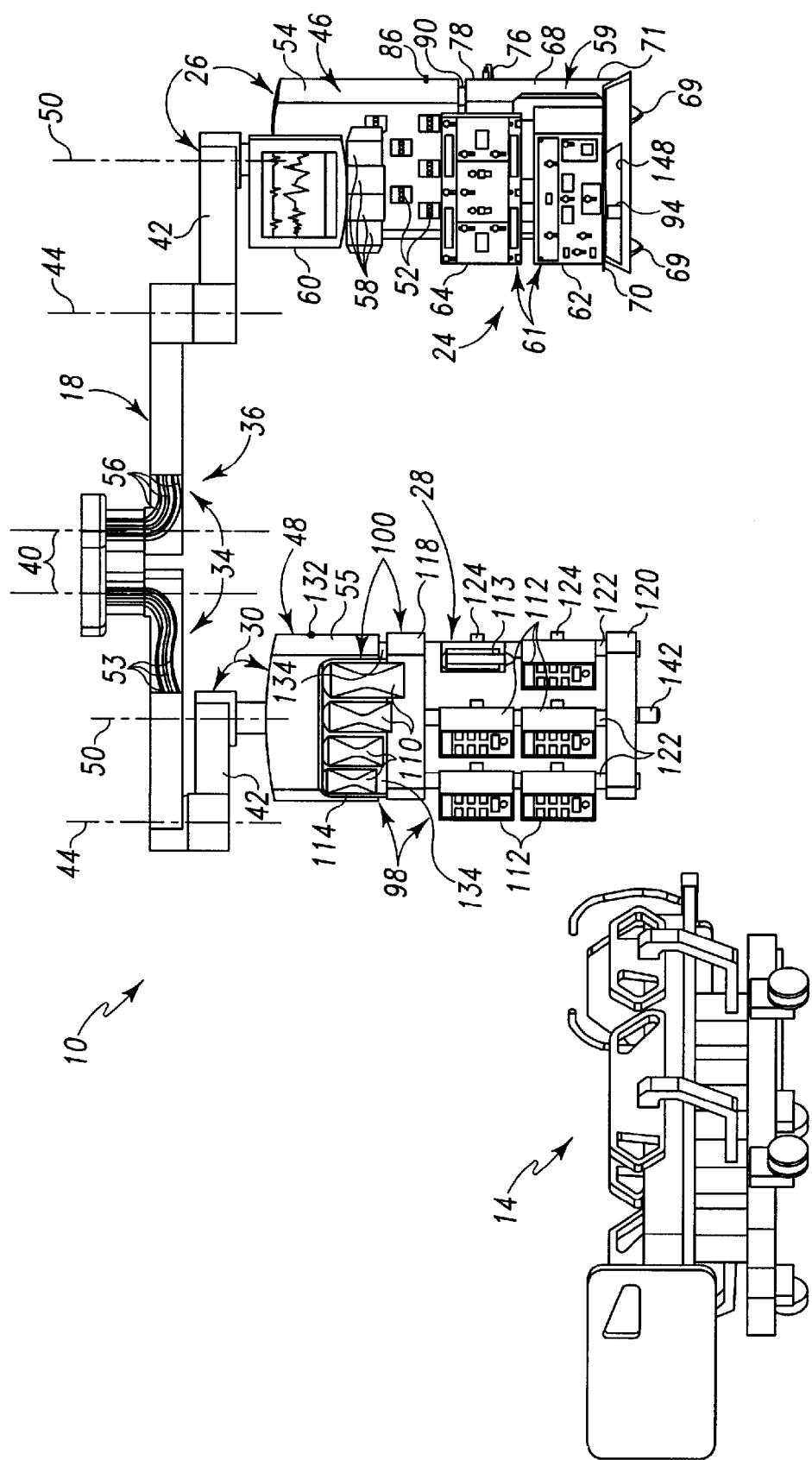
FIG. 1 is an elevation view of a patient care apparatus located in a hospital room to provide medical services for a patient (not shown) lying on a bed, the patient care apparatus having an overhead suspension system carrying a right ventilation unit having ventilation equipment and a left intravenous (IV) unit having IV equipment.

A patient care apparatus 10 shown in FIG. 1 is configured to be mounted in a hospital room, such as an intensive care room, to care for a patient lying on a patient support such as a hospital bed 14 in the room. Apparatus 10 has a suspension system 18 configured to be mounted to an overhead fixture such as a ceiling of the room to carry medical equipment to provide medical services for the patient. Suspension system 18 is further configured to carry a pair of stackable medical equipment modules or units 24, 28 which include medical equipment to provide medical services for the patient. Illustratively, unit 24 has ventilation equipment 61 and unit 28 has intravenous (IV) equipment 98. Thus, units 24, 28 can be referred to as a ventilation unit and an IV unit, respectively. It is within the scope of this disclosure for units 24, 28 to include other medical equipment in addition to or in place of ventilation and IV equipment 61, 98.

Units 24, 28 are detachable from suspension system 18 and unit 28 is stackable on top of unit 24 to provide a modular transport system 22, as shown, for example, in FIGS. 7–17. System 22 is configured to be attached to bed 14 to travel therewith to provide medical services for the patient if, for example, the patient needs to go to an operating room for surgery or to another room for patient diagnostic testing.

Suspension system 18 has relatively movable first and second carriers 26, 30, as shown in FIGS. 1–9. Unit 24 is attachable to and detachable from first carrier 26. Unit 28 is attachable to and detachable from second carrier 30.

Each carrier 26, 30 has a double-articulating arm unit 34. Arm units 34 cooperate to provide an overhead arm system 36 included in suspension system 18. Each arm unit 34 has an upper arm 38 and a lower arm 42. Each upper arm 38 is mounted to the ceiling for rotation about a first axis of rotation 40 (see FIG. 1). Each lower arm 42 is mounted to one of upper arms 38 for rotation about a second axis of rotation 44 (see FIG. 1). Carrier 26 has a first service column 46 suspended from lower arm 42 of carrier 26. Carrier 30 has a second service column 48 suspended from lower arm 42 of carrier 30. Each column 46, 48 is rotatable about a respective third axis of rotation 50 (see FIG. 1).

First column 46 has a housing 54 and a plurality of medical gas outlets 52 attached to a front face of housing 54, as shown in FIGS. 1–9. Carrier 26 has lines 56 routed from the ceiling through arms 38, 42 of carrier 26 into housing 54. Lines 56 include, for example, one or more medical gas lines for conducting medical gas (e.g., oxygen, air, vacuum) received from one or more hospital medical gas stations (not shown) to outlets 52 and one or more electrical lines attached to corresponding electrical outlets attached to housing 54. In some embodiments, one or more electrical power outlets (not shown) and/or data transmission outlets (not shown) are attached to housing 54 and corresponding lines 56.

Second column 48 has a housing 55 and a plurality of medical gas outlets 57 attached to a rear face of housing 55, as shown in FIGS. 6–9. Carrier 30 has lines 53 (see FIGS. 1–5) routed from the ceiling through arms 38, 42 of carrier 30 into housing 55. Lines 53 include, for example, one or more medical gas lines for conducting medical gas (e.g., oxygen, air, vacuum) received from one or more hospital medical gas stations to outlets 57 and one or more electrical lines. In some embodiments, one or more electrical power outlets (not shown) and/or data transmission outlets (not shown) are attached to housing 55 and corresponding lines 53.

Medical equipment is mounted to housing 54 of first column 46, as shown in FIGS. 1 and 2–9. Such medical equipment includes, for example, patient care modules 58 for receiving physiologic data from sensors (not shown) associated with the patient and a display 60 coupled to modules 58 for displaying the physiologic data. Such physiologic data includes, for example, electrocardiogram data, pulse oximetry, heart rate, respiration rate, and brain wave data. Lines (not shown) interconnect the sensors and modules 58. One or more of lines 56 supply electrical power for the electrical equipment mounted to housing 54.

Ventilation unit 24 has a ventilation equipment support module such as cart 59 attachable to and detachable from carrier 26 and ventilation equipment 61 carried by cart 59, as shown in FIGS. 1 and 3–5. Ventilation equipment 61 includes a ventilator 62 for assisting patient breathing, a ventilator control panel 64 for controlling ventilator 62, and a pair of oxygen tanks 66 for providing oxygen for the patient via ventilator 62. One or more fluid lines (not shown) lead from ventilator 62 to the patient. Ventilator 62 and ventilator control panel 64 are coupled together by one or more electrical or data transmission lines (not shown). Ventilator 62 and tanks 66 are also coupled together by one or more fluid lines (not shown). Ventilator 62 and control panel 64 receive electrical power from a battery contained in ventilator 62. In some embodiments, the battery receives electrical power from one or more electrical lines 53 routed from column 46 to the battery when ventilation unit 24 is connected to column 46. In other embodiments, ventilator 62 and control panel 64 receive electrical power from one or more of lines 53 routed from column 46 to ventilator 62 and control panel 64 when ventilation unit 24 is connected to column 46.

Figure 2:
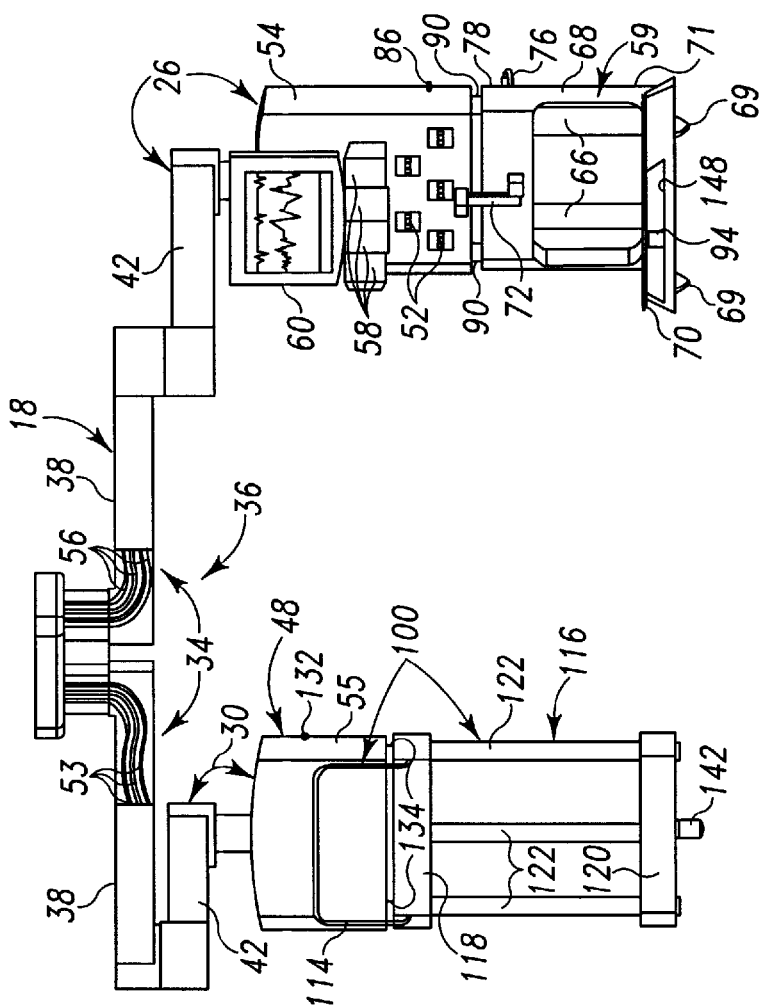
FIG. 2 is an elevation view of the patient care apparatus without the IV equipment and the ventilation equipment.
Figure 2:
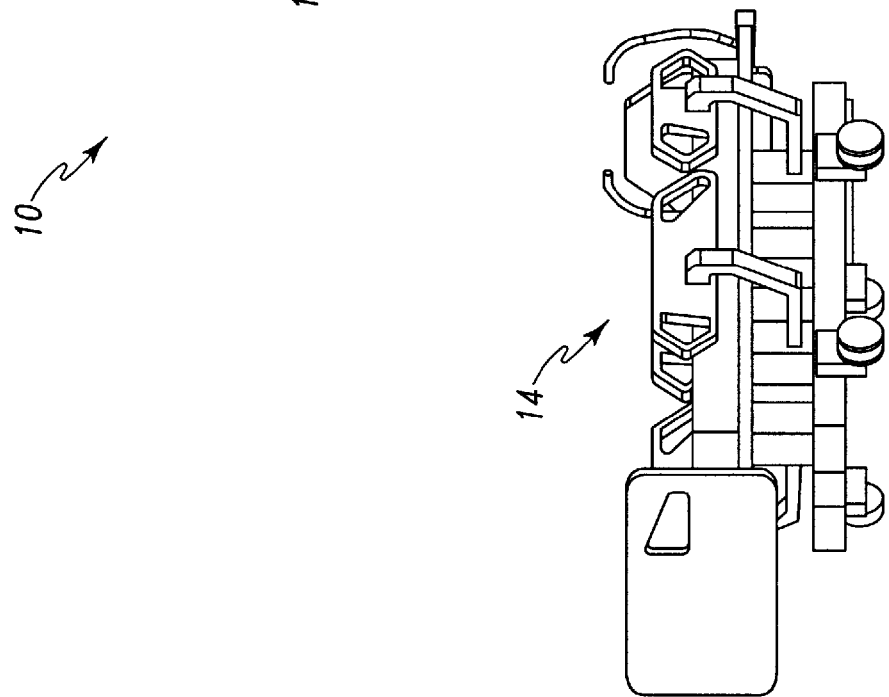
Figure 3:
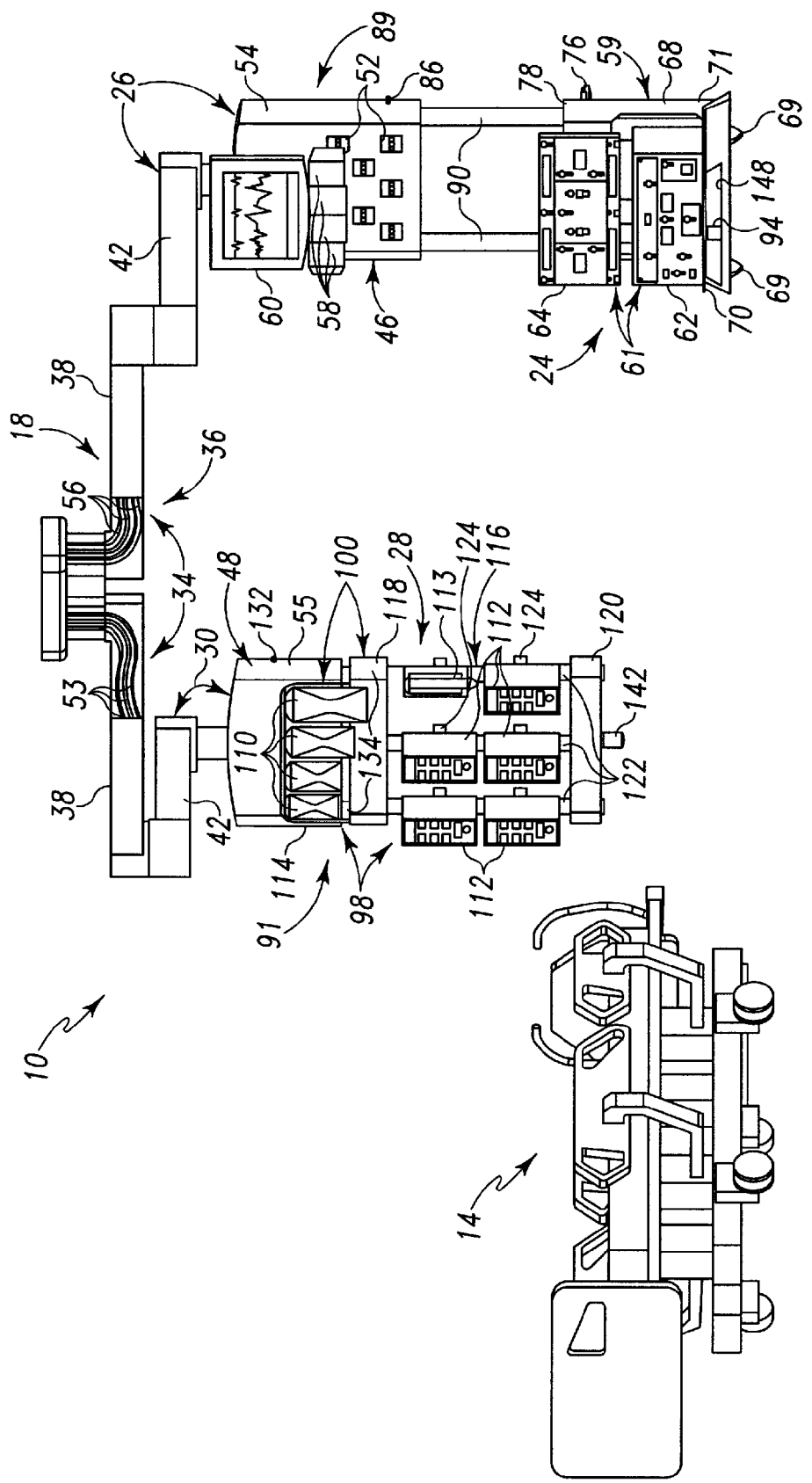
FIG. 3 is an elevation view showing vertical arms of the suspension system extended to lower the ventilation unit.
Figure 4:
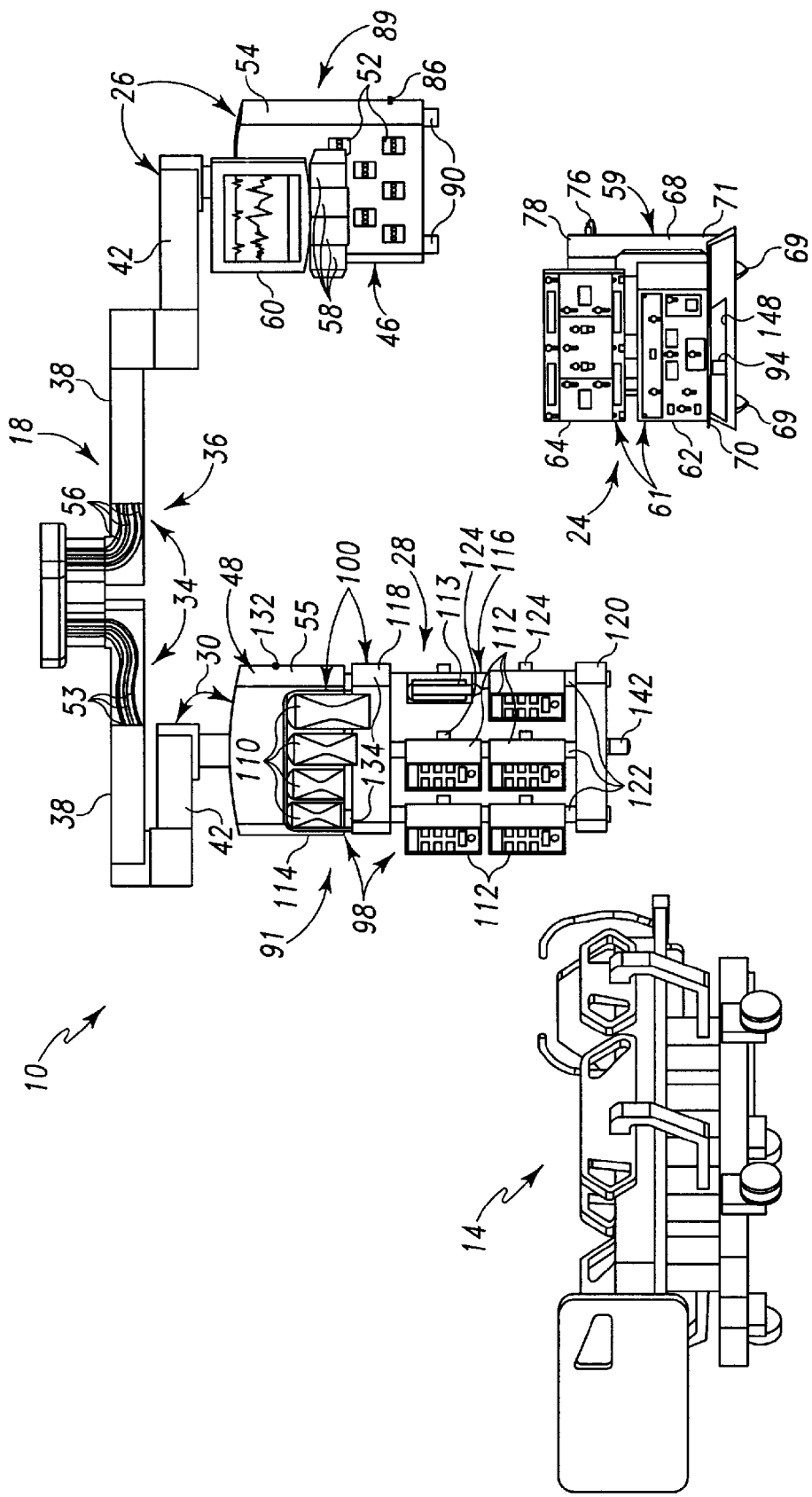
FIG. 4 is an elevation view showing the ventilation unit detached from the suspension system and the suspension system arms retracted.
Figure 5:
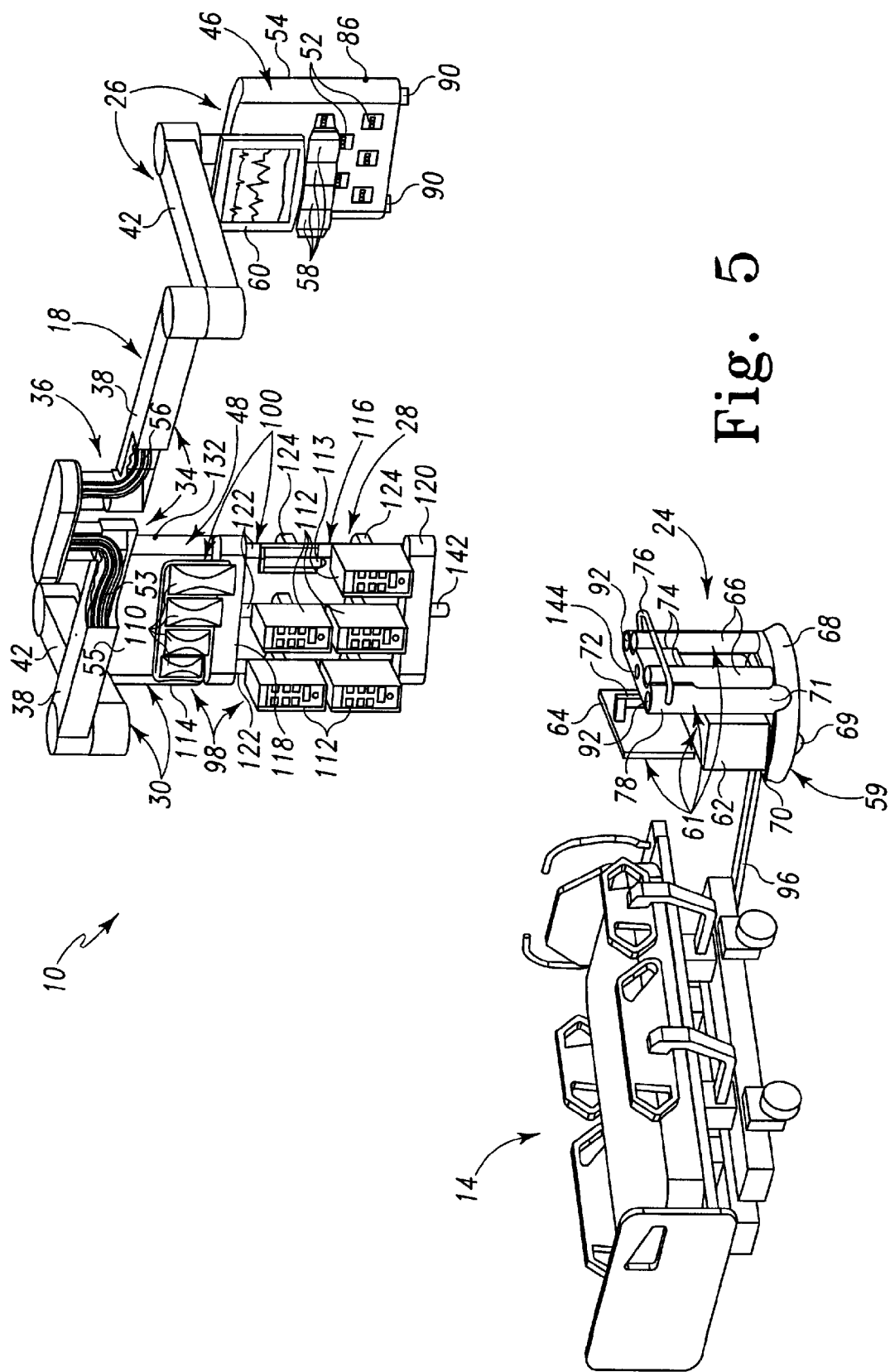
FIG. 5 is a perspective view showing the ventilation unit attached to the bed via a pivotable link.

Cart 59 has a frame 68, rolling elements 69 (e.g., casters or wheels) attached to a lower portion 71 of frame 68, a platform 70 attached to frame 68, and an adjustable arm 72 attached to frame 68, as shown, for example, in FIG. 2. Rolling elements 69 are spaced apart from a floor of the hospital room when cart 59 is suspended from carrier 26, as shown in FIGS. 1–3. Rolling elements 69 engage the floor to facilitate movement of unit 24 along the floor when unit 24 is detached from carrier 26, as shown in FIGS. 4–17. Ventilator 62 rests on platform 70, as shown, for example, in FIG. 10. Ventilator control panel 64 is mounted to arm 72.

Arm 72 is adjustable to move control panel 64 between various orientations. Exemplary orientations are shown in FIGS. 10–13. Ventilator control panel 64 is positionable, for example, above ventilator 62 (see FIG. 10), in front of ventilator 62 (see FIG. 11), to the left of ventilator 62 (see FIG. 12), and to the right of ventilator 62 (see FIG. 13).

The back of frame 68 is formed to include a pair of side-by-side, vertically extending tank-receiving receptacles 74, as shown, for example, in FIGS. 5–9. Each receptacle 74 is configured to receive and hold one of oxygen tanks 66 therein in an upright manner.

A handle 76 is attached to an upper portion 78 of frame 68, as shown, for example, in FIGS. 5–9. Handle 76 is gripped by a caregiver to maneuver unit 24 along the floor.

IV unit 28 has IV equipment 98 and an IV equipment support module such as a frame 100 for carrying IV equipment 98, as shown in FIGS. 1 and 3–13. IV equipment 98 includes a plurality of IV bags 110, a plurality infusion pumps 112, and a syringe-type infusion pump 113. Each IV bag 110 is associated with one of pumps 112, 113 via a line (not shown) to administer medicine to the patient. Each of pumps 112, 113 has its own battery for operation thereof. In some embodiments, one or more lines 53 are routed from second column 48 to pumps 112, 113 to supply electrical power thereto when IV unit 28 is attached to second column 48.

Frame 100 includes an IV bag support 114 and an infusion pump support 116, as shown in FIG. 2. Pump support 116 has a horizontal upper member 118, a horizontal lower member 120, and vertically extending, spaced-apart poles 122 interconnecting upper and lower members 118, 120. IV bag support 114 is mounted to upper member 118. IV bags 110 hang from bag support 114, as shown in FIGS. 1 and 3–13. Each pump 112, 113 is mounted to one of poles 122 by a coupler 124, as shown in FIGS. 6–9.

First column 46 has a first lifter 89 for raising and lowering ventilation unit 24 from and to the room floor. The first lifter 89 has a first driver (not shown) mounted within housing 54. The first lifter 89 also has a pair of vertically extending arms 90 (see FIGS. 3–4) operable to extend and retract from housing 54 in response to operation of the first driver. The first driver is in turn operable by an input control 86 (see FIGS. 1–9) which is attached to the housing 54. Control 86 may include a single control button, several control buttons, a toggle switch, or the like for controlling operation of the first driver and thus extension and retraction of arms 90.

The first driver includes, for example, a first electric motor coupled to one or more of lines 56 to receive electrical power therefrom. The first driver further includes first screw drive mechanisms coupled to the first motor and arms 90 to extend and retract arms 90.

A lower portion of each arm 90 is configured to be attached to upper portion 78 of frame 68 to suspend cart 59 from first column 46. Upper portion 78 is formed to include a pair of arm-receiving receptacles 92 (see FIGS. 5–6). Arms 90 are configured to attach to and detach from upper portion 78 of unit 24 via suitable coupling mechanisms. Lower ends of arms 90 are received in receptacles 92 when unit 24 is coupled to first column 46. Housing 54 matches the contour of upper portion 78 and a bottom surface of housing 54 overlies a top surface of upper portion 78 when the arms 90 suspend the cart 59 above the floor and adjacent to first column 46.

In some embodiments, there is only one arm 90 which is centrally located relative to housing 54 and is attachable to upper portion 78 of frame 100 via a plate or other suitable coupling mechanisms.

After unit 24 is detached from carrier 26, unit 24 can be attached to bed 14 for movement therewith, as shown, for example, in FIGS. 5–17, or unit 24 can be transported individually, if desired. If unit 24 is to be transported with bed 14, a caregiver uses handle 76 to maneuver unit 24 near bed 14 so that a connector such as a link 96 of bed 14 engages, latches onto, or otherwise couples to a post 94 of cart 59. Link 96 is pivotably coupled to a base of bed 14 to extend outwardly therefrom for attachment to post 94. Post 94 is attached to and extends upwardly from lower portion 71. Lower portion 71 has a cavity 148 formed therein to accommodate pivoting of link 96 relative to unit 24.

IV unit 28 is stackable on top of ventilation unit 24 for movement of both units 24, 28 together with bed 14 about the hospital. In this way, ventilation equipment 61 and IV equipment 98 remain close to the patient on bed 14 to provide medical services to the patient during transport of the patient throughout the hospital. Thus, a modular transport system 22 is provided when unit 28 is coupled to unit 24.

Second column 48 has a second lifter 91 for raising and lowering IV unit 28 off of and onto ventilation unit 24. Similar to the first lifter 89, the second lifter 91 has a second driver (not shown) mounted within housing 55. The second lifter 91 also has a pair of vertically extending arms 134 (see FIGS. 7–8) operable to extend and retract from housing 55 in response to operation of the driver. The second driver is, in turn, operable by an input control 132 (see FIGS. 1–9) which is attached to housing 55. Control 132 may include a single control button, several control buttons, a toggle switch, or the like for controlling operation of the driver and thus extension and retraction of arms 134.

The second driver includes, for example, a second electric motor coupled to one or more of lines 53 to receive electrical power therefrom. The second driver further includes one or more second screw drive mechanisms coupled to the second motor and arms 134 to extend and retract arms 134.

Figure 7:
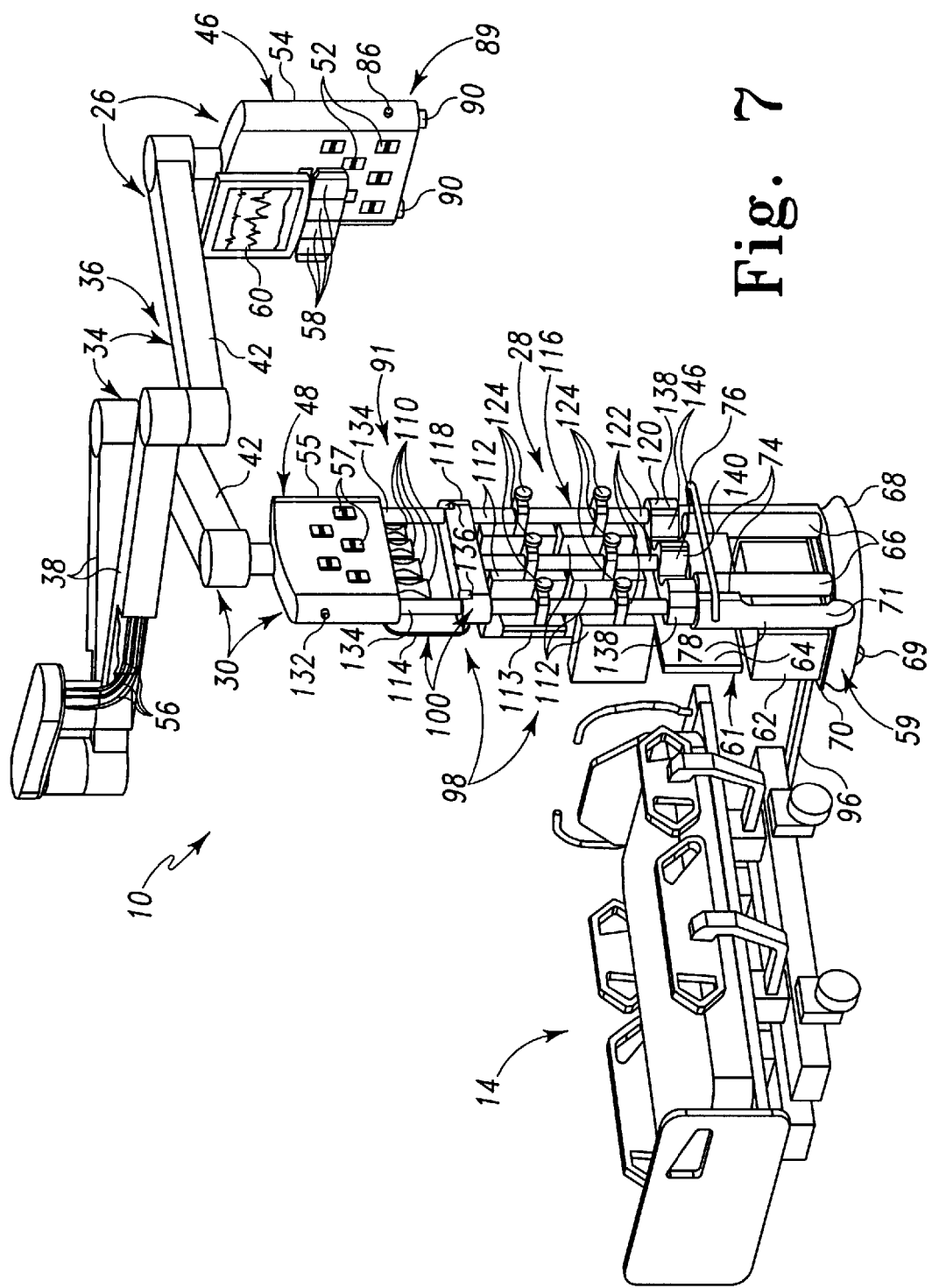
FIG. 7 is a perspective view showing vertical arms of the suspension system extended to lower the IV unit on top of the ventilation unit.
Figure 8:
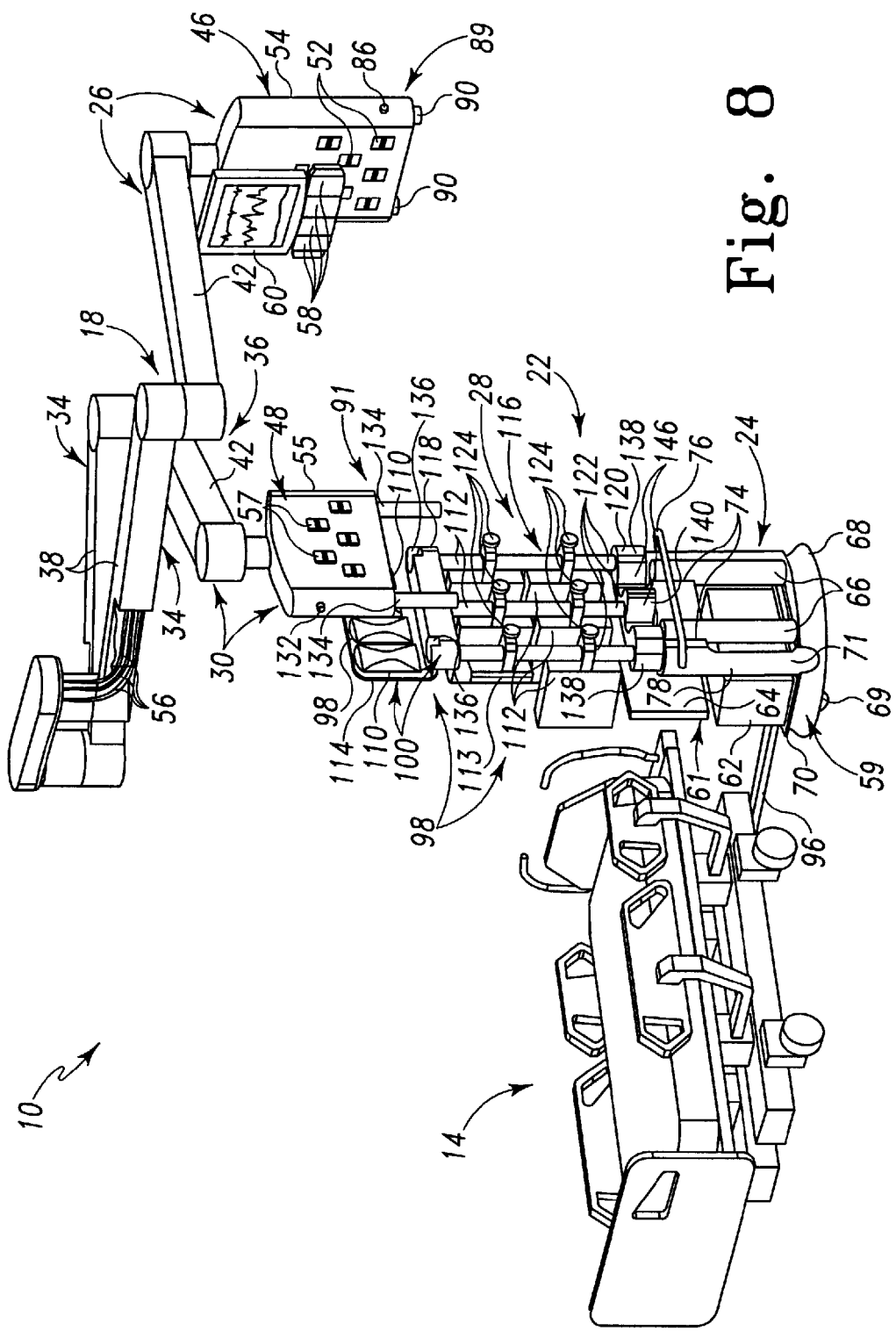
FIG. 8 is a perspective view showing the IV unit stacked on top of the ventilation transport system and the suspension system arms detached from the IV unit.
Figure 9:
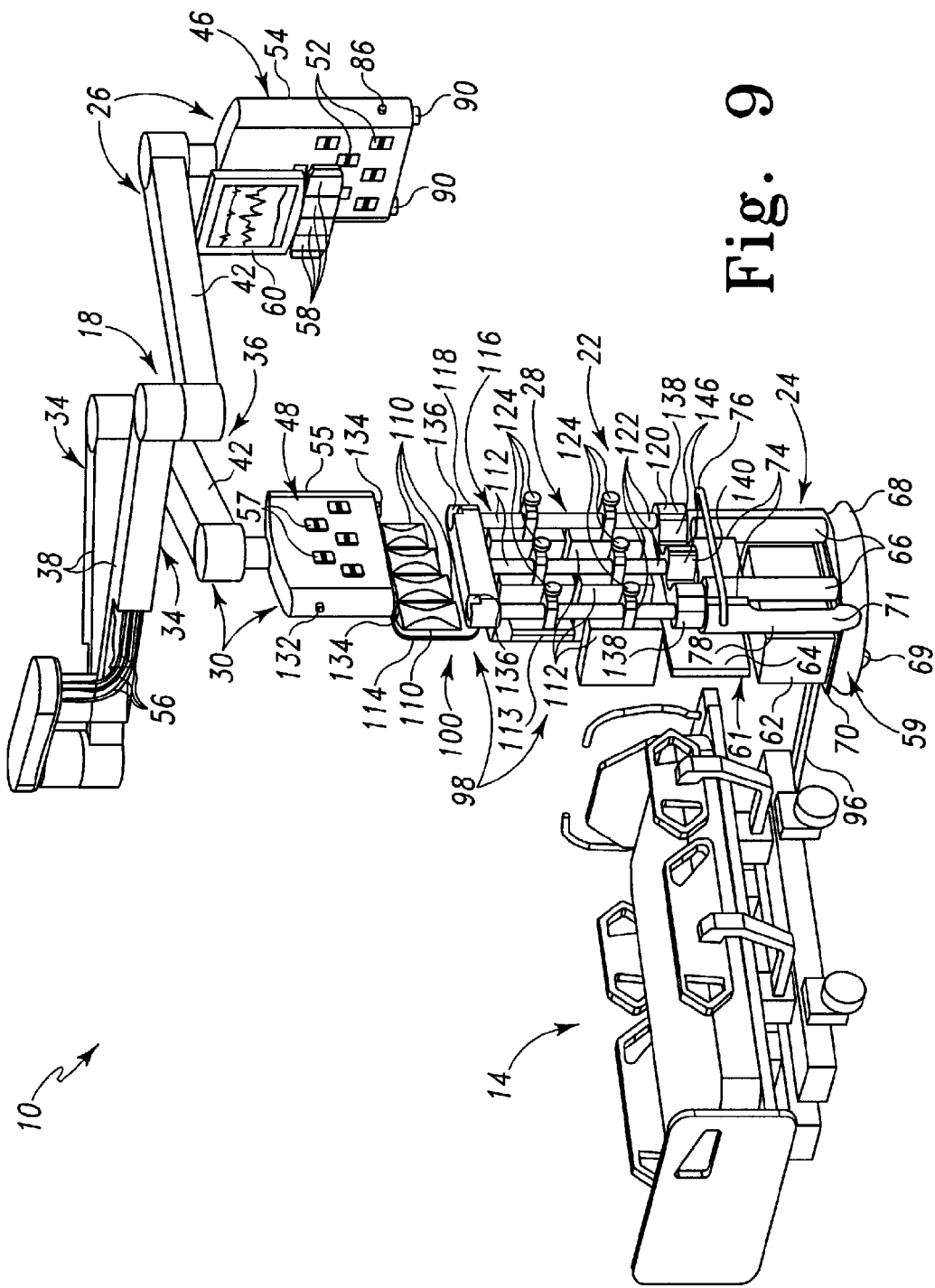
FIG. 9 is a perspective view showing the suspension system arms retracted after stacking the IV unit on top of the ventilation unit.
Figure 10:
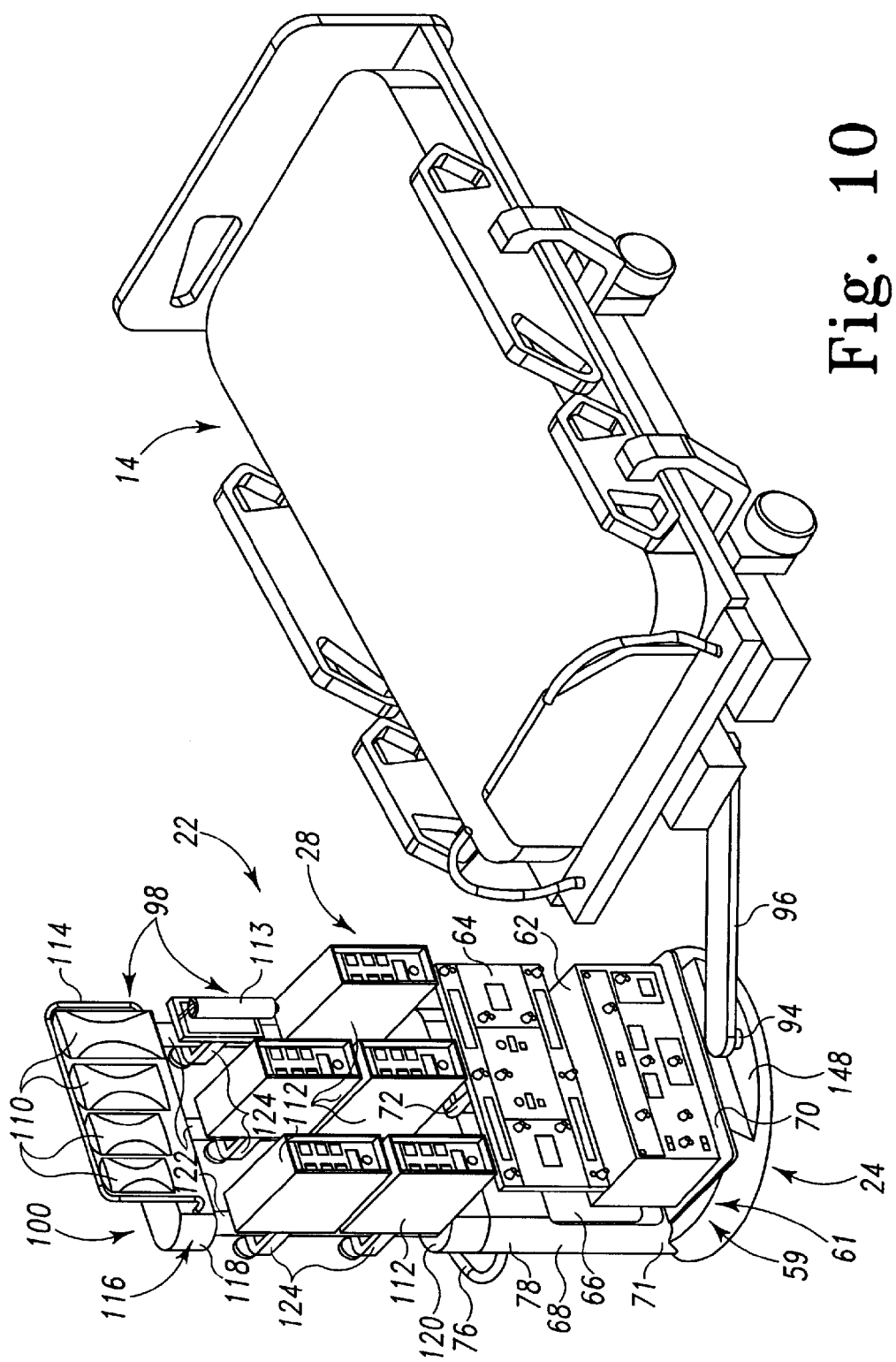
FIG. 10 is a perspective view showing a ventilator control panel of the ventilation unit positioned above a ventilator of the ventilation unit.
Figure 11:
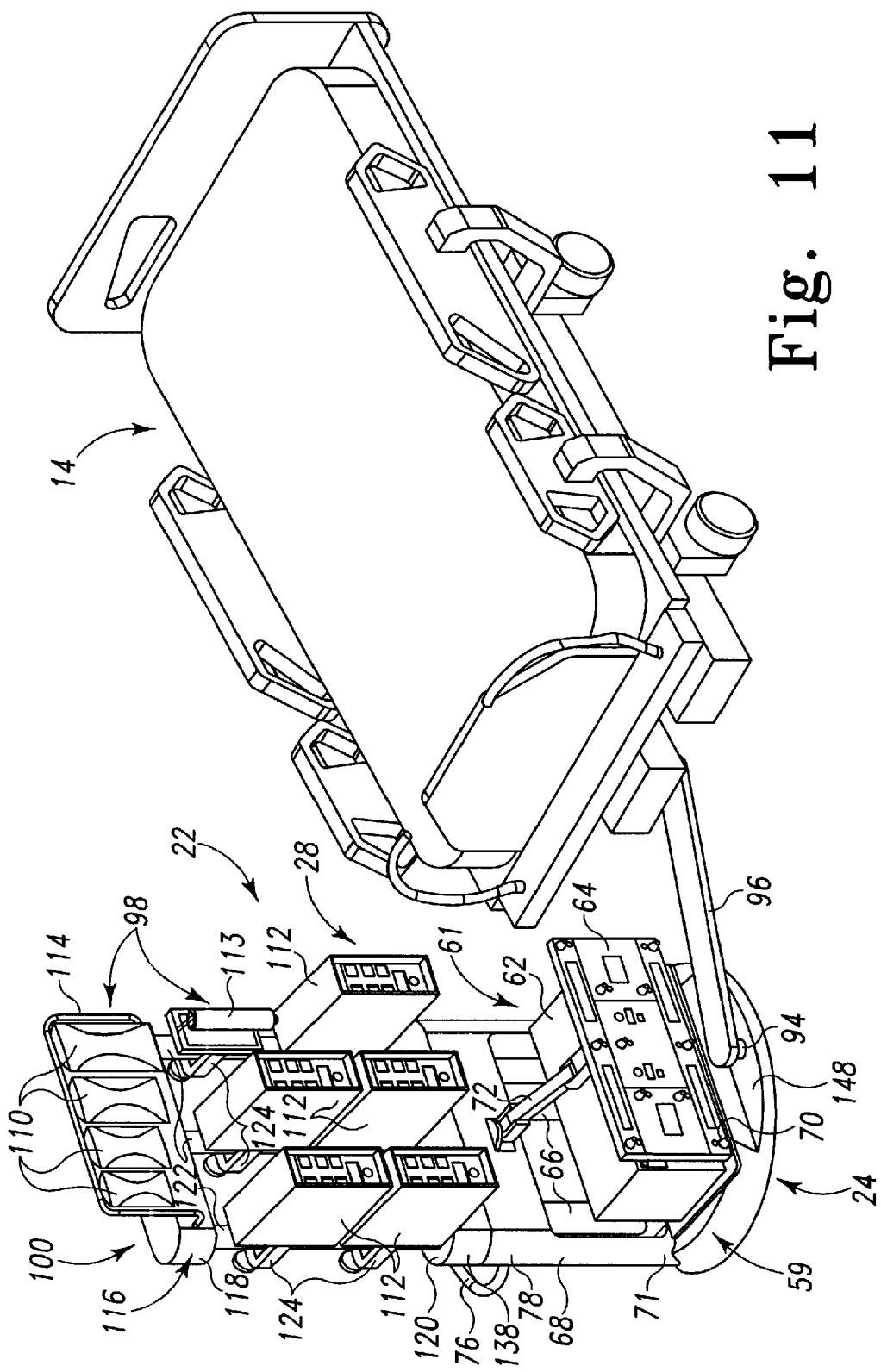
FIG. 11 is a perspective view showing the ventilator control panel positioned in front of the ventilator.
Figure 12:
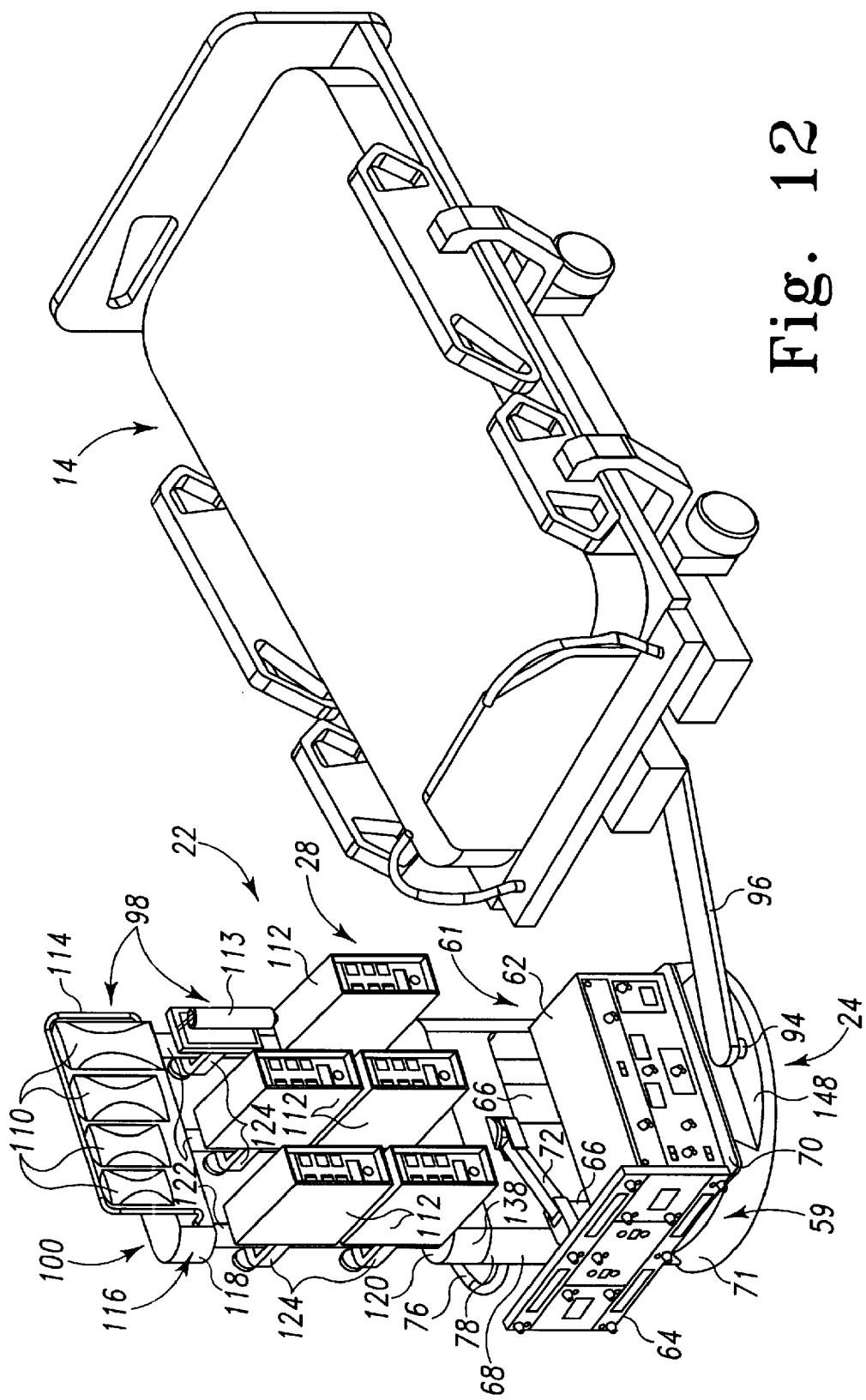
FIG. 12 is a perspective view showing the ventilator control panel positioned to the left of the ventilator.
Figure 13:
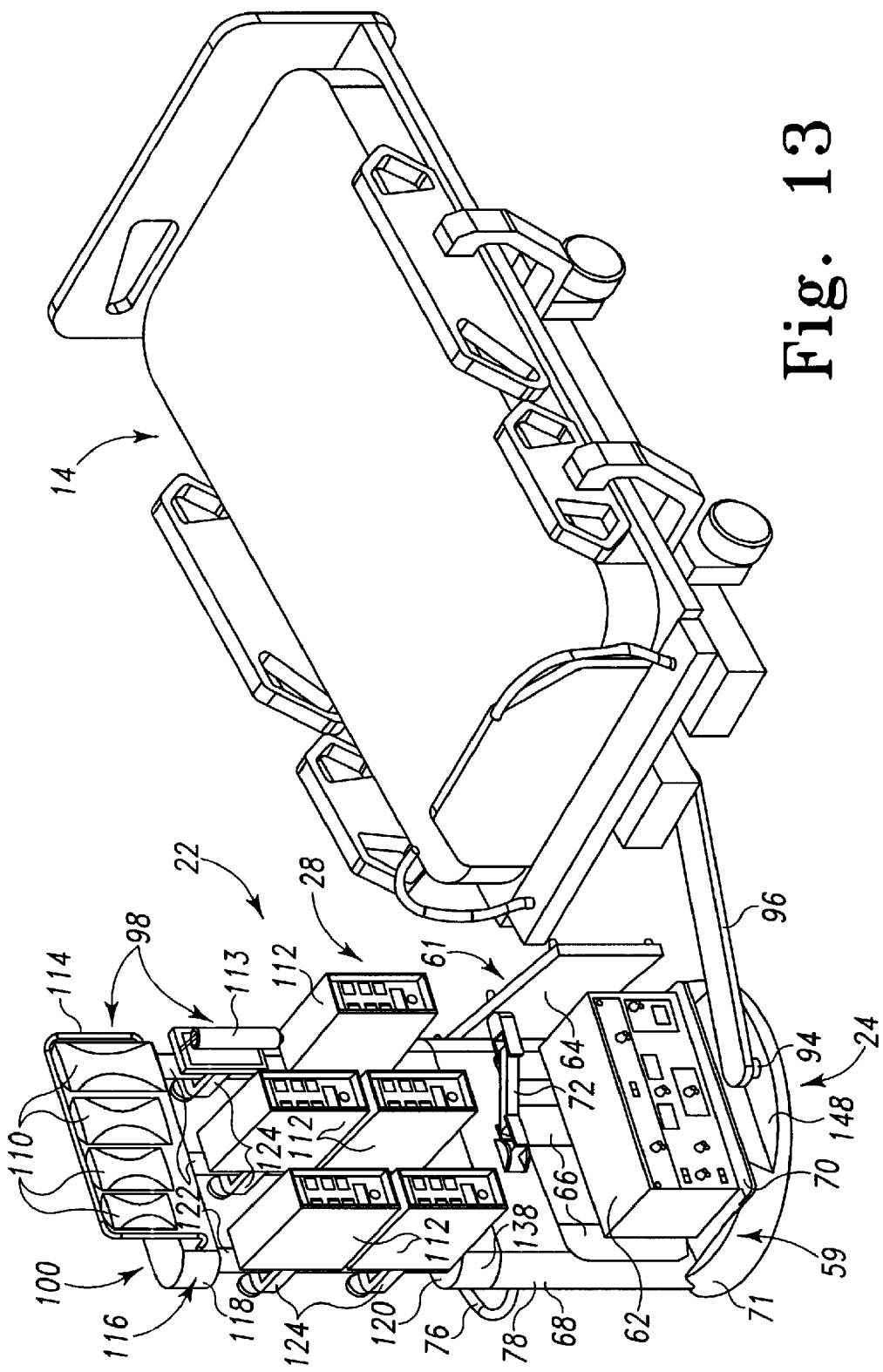
FIG. 13 is a perspective view showing the ventilator control panel positioned to the right of the ventilator.

A lower portion of each arm 134 is attached to upper member 118 to couple frame 100 to second column 48. Upper member 118 is formed to include a pair of receptacles 136. Arms 134 are configured to attach to and detach from upper member 118 via suitable coupling mechanisms. Lower ends of arms 134 are received in receptacles 136 when unit 28 is coupled to second column 48, as shown in FIG. 7, to raise and lower unit 28. After arms 134 lowers unit 28 onto unit 24, arms 134 can be detached from upper member 118, as shown in FIG. 8, to allow arms 134 to be retracted without unit 28 attached thereto, as shown in FIG. 9. Housing 55 matches the contour of upper member 118 and a bottom surface of housing 55 overlies a top surface of upper member 118 when the arms 134 suspend the frame 100 above the floor and adjacent to second column 48.

In some embodiments, there is only one arm 134 which is centrally located relative to housing 55 and is attachable to upper member 118 via a plate or other suitable coupling mechanisms.

Figure 6:
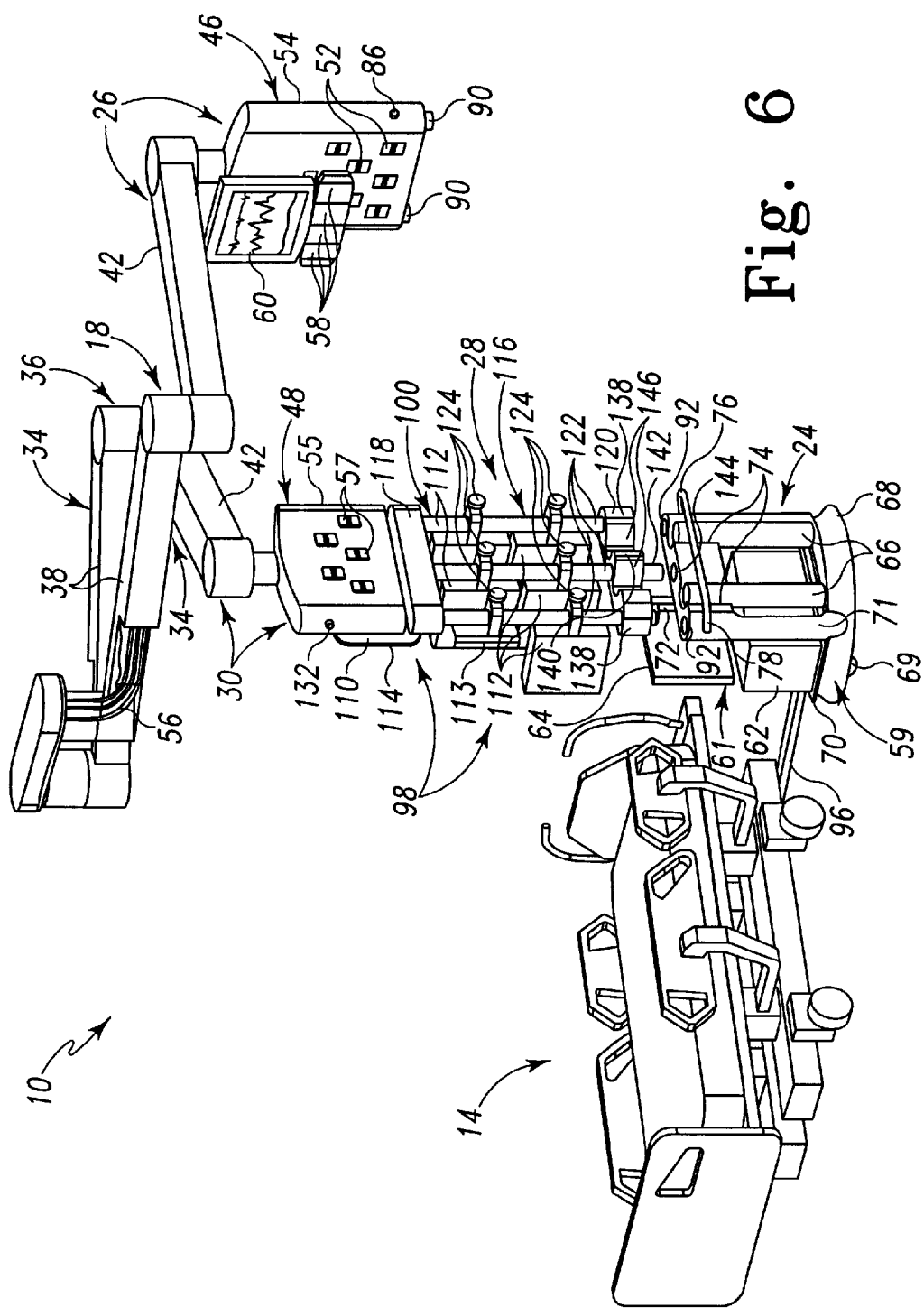
FIG. 6 is a perspective view showing the suspension system positioning the IV unit directly above the ventilation unit.

To stack unit 28 on top of unit 24, carrier 30 is moved to position unit 28 directly above unit 28, as shown in FIG. 6. The caregiver activates control 132 to lower unit 28 onto cart 59.

When frame 100 is placed on cart 59, lower member 120 of frame 100 is attached to upper portion 78 of cart 59. The contours of lower member 120 and upper portion 78 match one another when frame 100 is placed on cart 59. Lower member 120 has side connector portions 138 and an intermediate connector portion 140 located between side connector portions 138, as shown in FIGS. 6–9. Intermediate connector portion 140 has a downwardly extending post 142, as shown in FIGS. 1–6. When unit 28 is lowered onto unit 24, portions 138, 140 rest on an upper surface of upper portion 78 and a middle receptacle 144 formed in upper portion 78 receives post 142. Lower member 120 further has receptacles 146 to accommodate outlet hardware and gauges attached to the upper ends of tanks 66.

The caregiver then detaches arms 134 from receptacles 136 of upper member 118, as shown in FIG. 8, and activates control 132 to raise arms 134 into housing 55, as shown in FIG. 9. Units 24, 28 thus stacked provide a modular transport system 22 to provide medical service to the patient on bed 14 during transport of the patient.

Link 96 is pivotable relative to bed 14 to allow transport system 22 to be positioned at different locations relative to bed 14 to facilitate transport of the patient throughout the hospital. For example, system 22 can be located adjacent a side of bed 14 (see FIGS. 9 and 17), adjacent a corner of bed 14 (see FIGS. 10–13), and adjacent an end of bed 14 (see FIGS. 14–16). Once system 22 is positioned in a desired position relative to bed 14, link 96 can be locked so that system 22 is stationary relative to bed 14.

Figure 14:
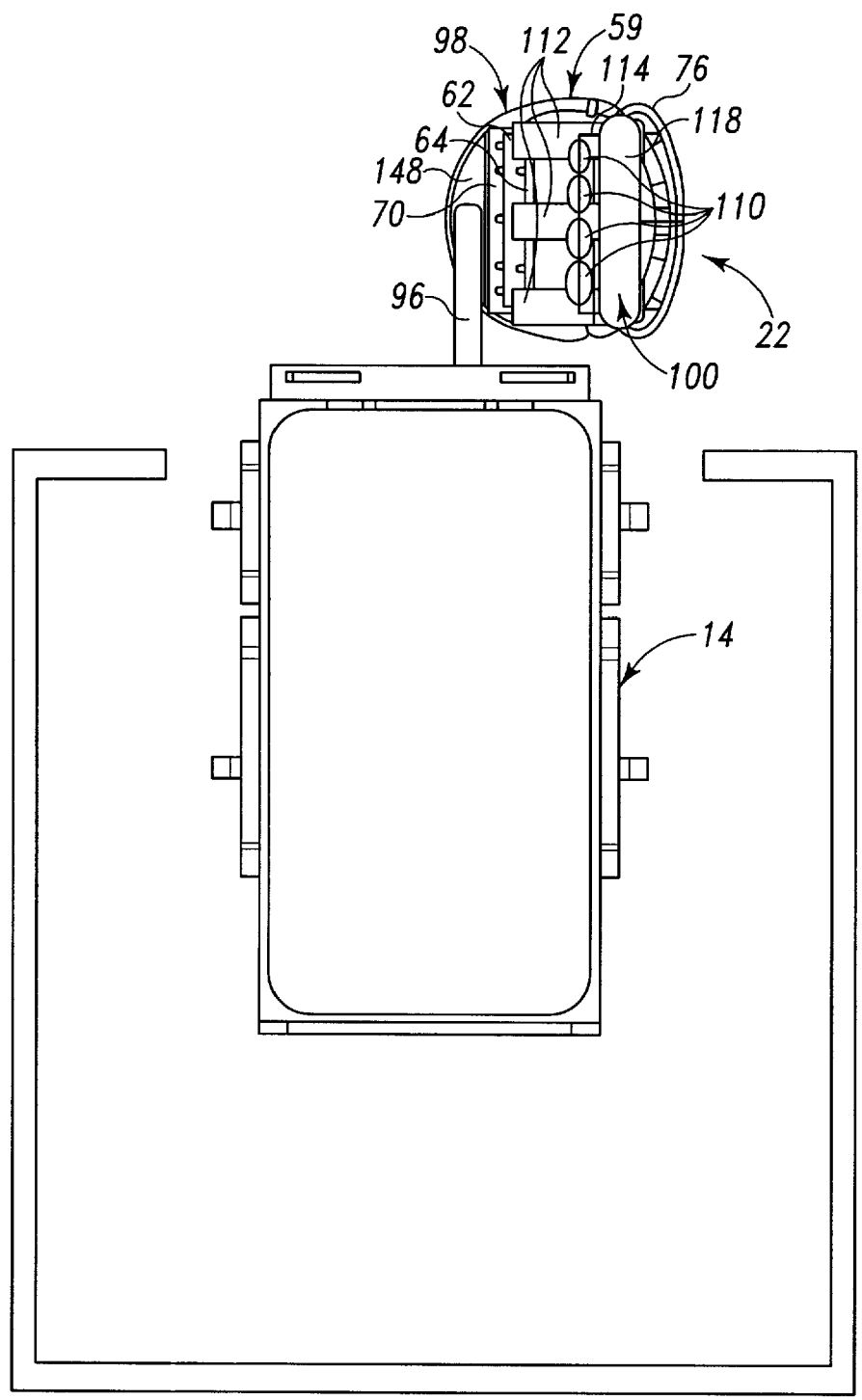
FIGS. 14–17 are top plan views showing maneuvering of the IV and ventilation units and the bed into a confined area such as an elevator.
Figure 15:
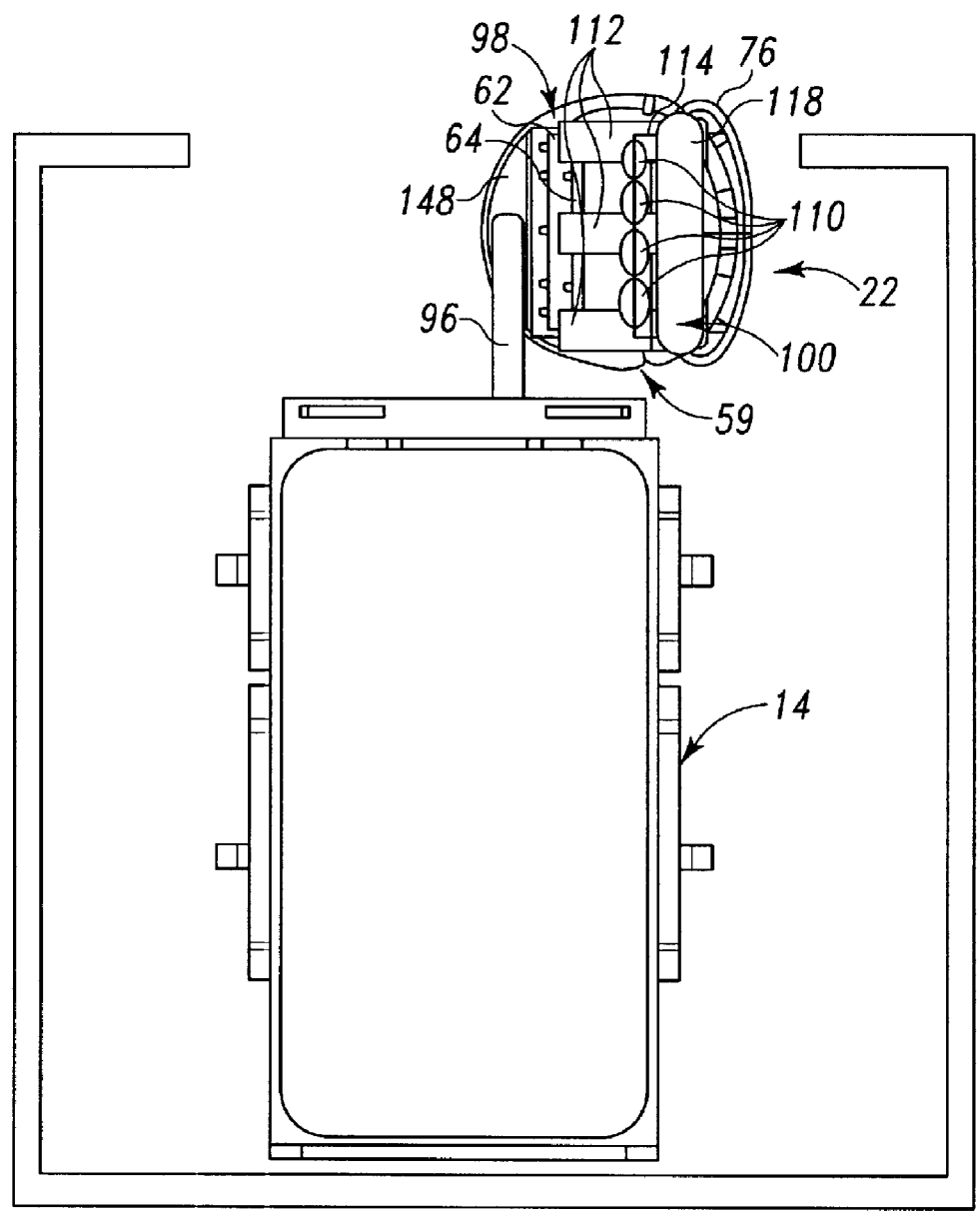
Figure 16:
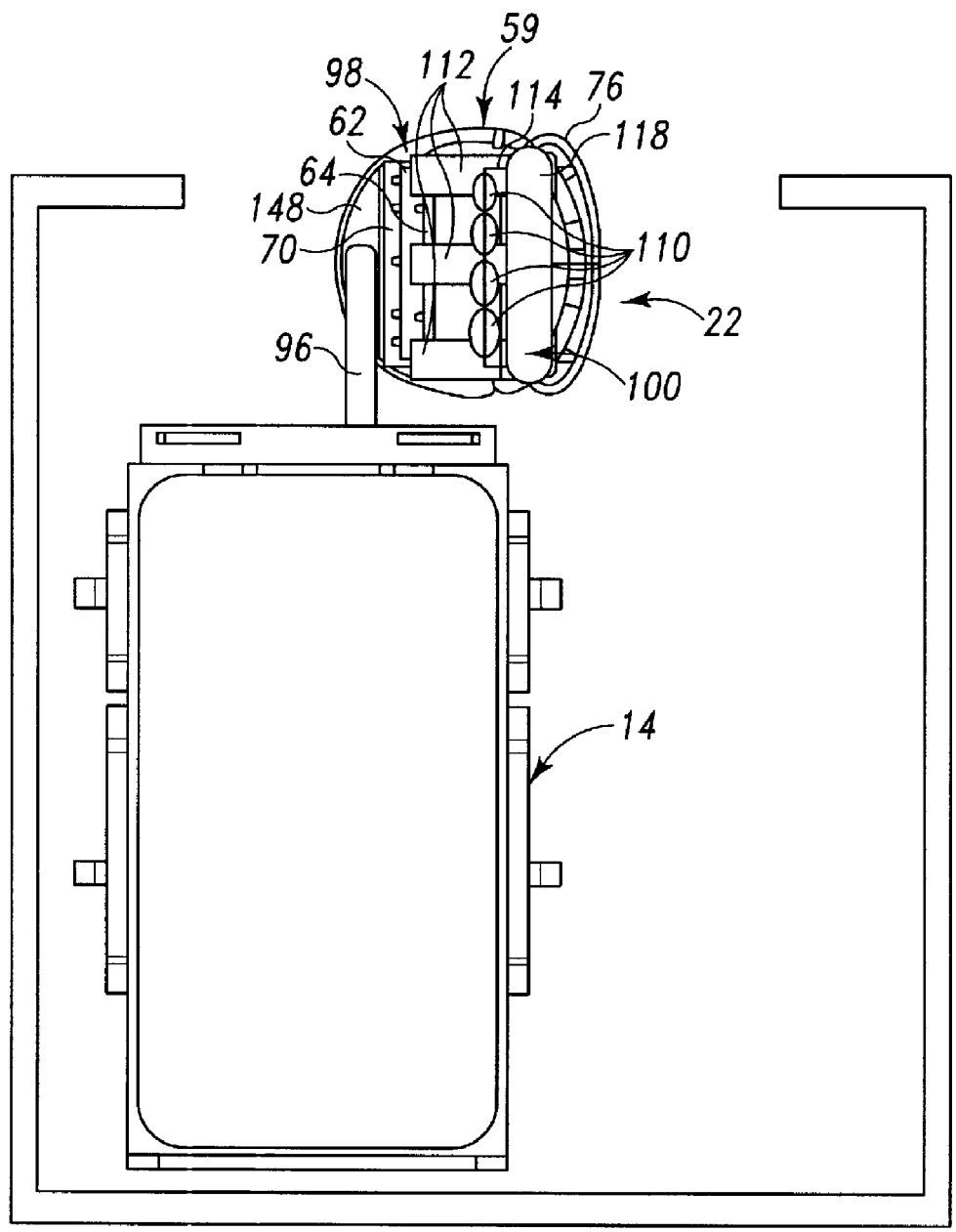
Figure 17:
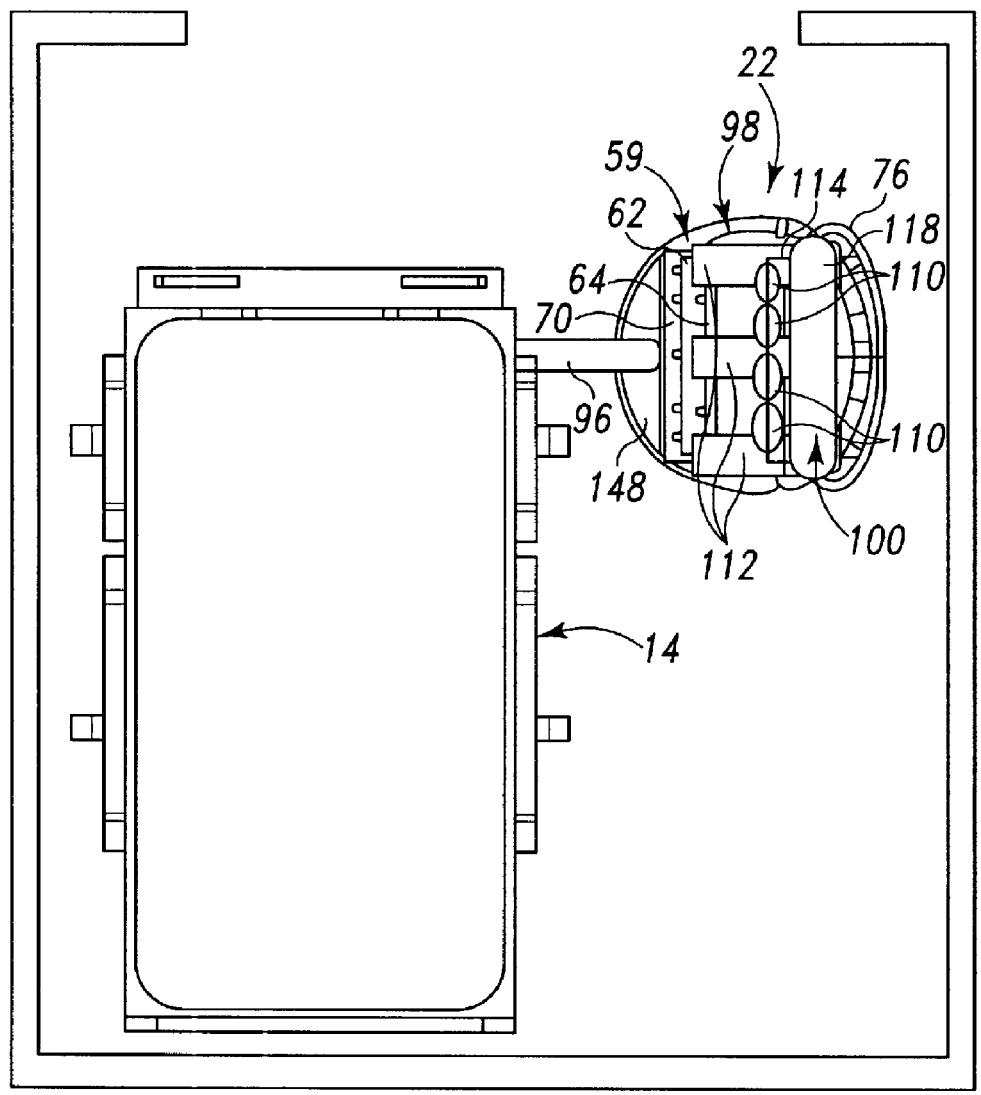

The position of system 22 is adjusted relative to bed 14 when, for example, system 22 and bed 14 are located in a confined area such as an elevator 142, as shown in FIGS. 14–17. During entry of system 22 and bed 14 into elevator 142, system 22 is positioned, for example, at an end of bed 14 when system 22 and bed 14 enter elevator 142, as shown in FIGS. 14–16. Once system 22 and bed 14 are positioned in elevator 142, system 22 is moved to the side of bed 14 to fit into elevator 142, as shown in FIG. 17.

Although the apparatus for carrying medical equipment has been described in detail with reference to a certain illustrative embodiment, variations and modifications exist within the scope and spirit of this disclosure as described and defined in the following claims.

The invention claimed is:

1. A patient care apparatus comprising
  a suspension system and
  a pair of modules attached to different portions of the suspension system, and coupleable together to form a cart to be moved to a different location.

2. The patient care apparatus of claim 1, wherein the suspension system is configured to move a first module of the pair of modules between a raised position suspended above a floor and a lowered position on the floor.

3. The patient care apparatus of claim 2, wherein the suspension system is configured to move a second module of the pair of modules between an upper position suspended above the floor and a lower position in which the second module is coupleable to the first module.

4. The patient care apparatus of claim 3, wherein the suspension system comprises a first lifter to move the first equipment support module between the raised and lowered positions and a second lifter to move the second equipment support module between the upper and lower positions.

5. The patient care apparatus of claim 1, wherein the pair of modules are stacked when coupled together to form the cart.

6. The patient care apparatus of claim 1, wherein the suspension system comprises a first vertically movable arm and a second vertically movable arm, a first module of the pair of modules is coupled to the first vertically movable arm, and a second module of the pair of modules is coupled to the second vertically movable arm.

7. The patient care apparatus of claim 1, wherein the suspension system comprises a first service column to which a first module of the pair of modules is coupleable and a second service column to which a second module of the pair of modules is coupleable.

8. The patient care apparatus of claim 1, wherein the suspension system comprises at least one arm to which the pair of modules are coupleable and the at least one arm is adapted to couple to a ceiling for pivoting movement.

9. The patient care apparatus of claim 1, wherein the suspension system comprises a pair of arm assemblies and each module of the pair of modules is coupleable to a respective one of the arm assemblies.

10. The patient care apparatus of claim 9, wherein the suspension system further comprises a pair of service columns and each service column of the pair of service columns is coupled to a respective one of the arm assemblies.

11. The patient care apparatus of claim 1, wherein at least one of the pair of modules is configured to carry at least one of IV equipment and ventilation equipment.

12. A patient care apparatus comprising
a first arm assembly,
a second arm assembly,
a first module coupleable to the first arm assembly, the first module having a set of wheels that engage a floor when the first module is decoupled from the first arm assembly, and
a second module coupleable to the second arm assembly, the second module being decoupleable from the second arm assembly and coupleable to the first module to form a cart to move the modules to a different location.

13. The patient care apparatus of claim 12, wherein one of the first and second modules has a cavity and the other of the first and second modules has a connector that is received in the cavity when the second module is stacked on top of the first module.

14. The patient care apparatus of claim 12, wherein the first arm assembly includes a first lifter that is operable to raise and lower the first module.

15. The patient care apparatus of claim 14, wherein the first arm assembly comprises a first service column and the first lifter extends and retracts from the first service column.

16. The patient care apparatus of claim 14, wherein the second arm assembly includes a second lifter that is operable to raise and lower the second module.

17. A patient care apparatus for use in a room comprising a ceiling, the patient care apparatus comprising
a suspension system comprising a first arm system to be attached to the ceiling, a second arm system to be attached to the ceiling, a first service column depending from the first arm system, a second service column depending from the second arm system, a first lifter attached to the first service column, and a second lifter attached to the second service column,
a first equipment support module configured to support equipment for care of a patient and comprising a rolling element to facilitate movement of the first equipment support module along a floor and an upper portion to be attached to and detached from the first lifter, and
a second equipment support module configured to support equipment for care of the patient and to be attached to and detached from the second lifter, the first lifter being configured to move the first equipment support module between an upper position suspended above the floor and a lower position in which the rolling element engages the floor, the second lifter being configured to move the second equipment support module between upper and lower positions suspended above the floor, the first equipment support module and the second equipment support module being configured for stacking the second equipment support module on top of the upper portion of the first equipment support module when the upper portion of the first equipment support module is detached from the first lifter and the second lifter lowers the second equipment support module onto the upper portion of the first equipment support module.

18. The patient care apparatus of claim 17, wherein each service column comprises a medical gas service outlet.

19. The patient care apparatus of claim 17, wherein the first equipment support module is configured to carry ventilation equipment and the second equipment support module is configured to carry IV equipment.

20. The patient care apparatus of claim 17, wherein the first and second equipment support modules form a cart when the second equipment support module is stacked on the first equipment support module and the cart is adapted to be coupled to a movable patient support to be moved in unison with the patient support.

* * * * *